May 30, 1967 W. E. LAMMERTS Plant Pat. 2,744
LILAC PLANT
Filed Aug. 9, 1965
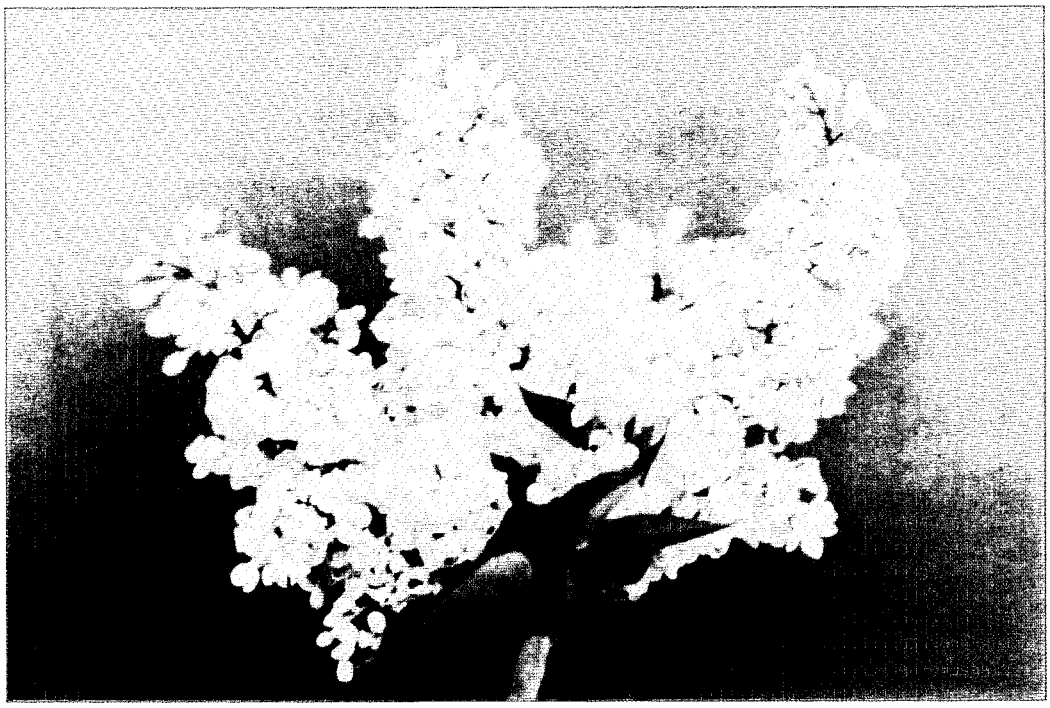
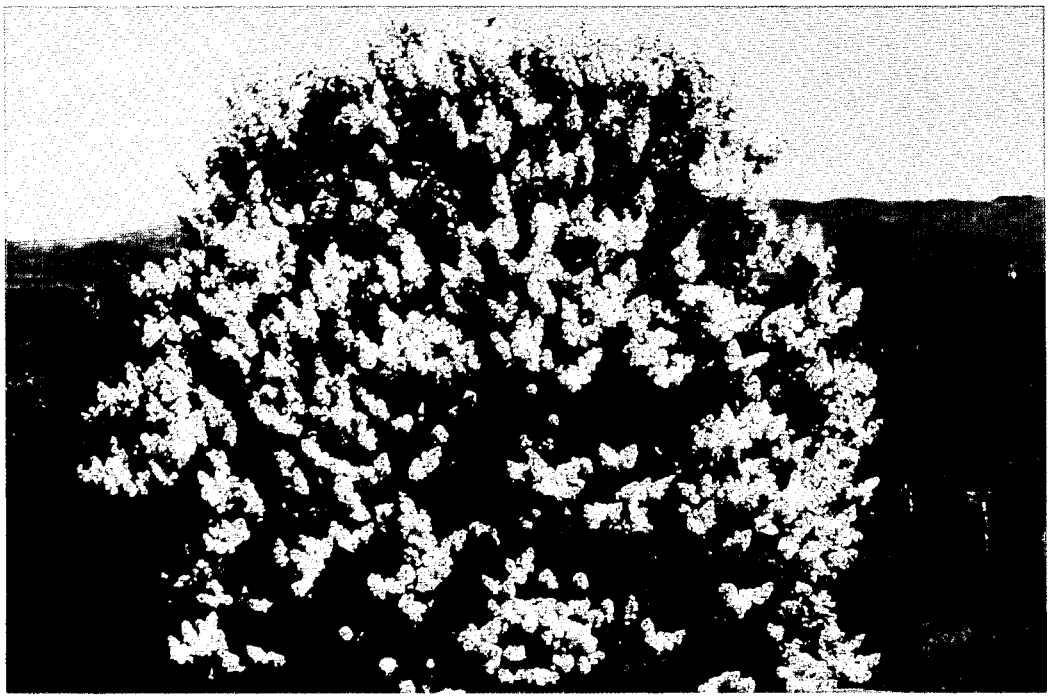

United States Patent Office

Plant Pat. 2,744
Patented May 30, 1967

2,744
LILAC PLANT

Walter E. Lammerts, Livermore, Calif., assignor to General Bionomics, Inc., Santa Rosa, Calif.

Filed Aug. 9, 1965, Ser. No. 479,698
1 Claim. (Cl. Plt.—66)

The invention relates to a new and distinct variety of lilac plant of the French hybrid class, orginated by me in May 1960 as a consequence of a breeding program begun in 1959. The parentage of my new lilac plant is as follows:

Unnamed large flowered, broad petaled, white seedling #P65, the seed parent, × unnamed profuse blooming, white seedling, the pollen parent.

The object of the cross was the production of a profusely blooming white lilac of the French hybrid type with large compound thyrses, large florets with broad petals, well spaced in the inflorescence, borne on a plant which leafed out and flowered well under mild climatic conditions under which lilacs generally do not flower well. These objectives were achieved along with other desirable improvements, as evidenced by the following unique combination of characteristics which are outstanding in the new variety and which distinguish it from its parents as well as from all other varieties of which I am aware. My new variety is primarily characterized by:

An unusually long life of the bloom on the plant and as a cut flower, an ability to leaf out and flower well at the proper time of year under unusually mild climatic conditions such as prevail in coastal California, especially south of Marin County, Calif.; a dense, compact, rounded habit of growth that is vigorous but uniform; a large compound thyrse bearing fragrant, white flowers of large size and having large, very broad corolla lobes and with the individual florets well spaced in the inflorescence; and by its adaptability to irrigated culture.

A sexual reproduction of my new variety by budding on *Ligustrum ovalifolium*, through a series of annual propagations at Livermore, Calif., shows that all characteristics of the variety come true to form through succeeding propagations. The accompanying photographs illustrate the primary characteristics of my new variety as nearly true as is reasonably possible to make them with presently available techniques.

The following botanical description is based upon observation of the original seedling grown under garden conditions at Livermore, Calif. and two year budded plants grown in containers at Santa Rosa, Calif.

Plant large, rounded, compact. Growth vigorous, uniform over the entire surface of the plant. Plant never open at the bottom, but spreading from the ground upward, no pronounced terminal axial dominance; free from vigorous leader growth. Stems stout, grey, internodes relatively short, producing compact growth in spite of the pronounced vigor. Leaves large, medium green, leafing out well even under mild winter conditions, leaves well developed at anthesis. The inflorescence is a large compound thyrse 7″–9″ high by 7″–12″ wide, exceeding in size and number of florets the varieties "Katherine Havemeyer," "White Hyacinth," "Monument," "Vestal," and all other common varieties of white lilacs of the French hybrid type known to me. Blooming period at Livermore was March 15–April 18 in 1963, in full flower Apr. 1, 1963. Blooming ordinarily begins within 2–3 weeks after the advent of frost-free weather at Livermore and Santa Rosa. The flower morphology is characteristic of the genus. The flower bud is large, tubed, globular, ivory-cream to greenish-white. The calyx lobes are about 1/32″ long by about as wide. The calyx tube is about 1/16″ long and about as wide. The Corolla is single, white, from 7/8″–1 1/8″ across, long tubed, the tube about 7/16″ long. The lobes of the corolla are patent, large and broad, obovate, accuminate, about 1/4–3/8″ wide by 3/8–5/8″ long. The corolla has remarkable substance and remains in a fresh condition from 7–10 days after anthesis on the plant and 6–8 days as a cut flower. The durability of the bloom exceeds other white lilacs by 3–4 days, and most other varieties known to me by 2–3 days. The stamens are characteristic of the genus, the style is about 1/4″ long and the stigmas about 1/16″ long on separation.

The variety is self fertile, producing an abundance of open pollenated seed. The capsules are characteristic of the genus, 1 to 4 seeded, generally 3 or 4 seeded.

Having thus disclosed my invention, I claim:

A new and distinct variety of lilac plant of the French hybrid class substantially as herein shown and described, primarily characterized by: An unusually long life of the bloom on the plant and as a cut flower, an ability to leaf out and flower well and at the proper time of year under unusually mild climatic conditions such as prevail in coastal California, especially south of Marin County, Calif.; a dense, compact, rounded habit of growth that is vigorous but uniform; a large compound thyrse bearing fragrant white flowers of large size and having large broad petals, and with the individual florets well spaced in the inflorescence; and by its adaptability to irrigated culture.

No references cited.

ABRAHAM G. STONE, *Primary Examiner.*
ROBERT E. BAGWILL, *Examiner.*